United States Patent [19]
Majlessi

[11] Patent Number: 5,360,427
[45] Date of Patent: Nov. 1, 1994

[54] RETRACTABLE ELECTRO-SUCTION DEVICE

[76] Inventor: Heshmat Majlessi, 233 Purchase St., Rye, N.Y. 10580

[21] Appl. No.: 999,693

[22] Filed: Dec. 18, 1992

[51] Int. Cl.⁵ .............................................. A61B 17/39
[52] U.S. Cl. ...................................... 606/41; 606/42; 606/45; 606/39
[58] Field of Search ................. 606/32, 37, 39, 40, 606/41, 42, 45, 48

[56] References Cited

U.S. PATENT DOCUMENTS

| | | | |
|---|---|---|---|
| 4,562,838 | 1/1986 | Walker | 606/42 |
| 5,035,695 | 7/1991 | Weber, Jr. et al. | 606/42 |
| 5,071,418 | 12/1991 | Rosenbaum | 606/42 |
| 5,100,402 | 3/1992 | Fan | 606/41 |

*Primary Examiner*—Stephen C. Pellegrino
*Assistant Examiner*—Sonya C. Harris
*Attorney, Agent, or Firm*—Lackenbach, Siegel, Marzullo, Aronson, & Greenspan

[57] ABSTRACT

An electro cautery device for attachment to a suction pump and to a source of electric current includes a tubular member one end of which is connectable to the suction pump and the other end is insertable into the cavity of a human torso. A retractable cautery element is mounted on the end insertable into the torso and connectable to a source of electric current. The cautery element is movable between a retracted position which prevents it from being exposed to tissue and an extended position used during cauterization. A button on the tubular member moves the cautery element from the retracted to the extended positions when depressed, simultaneously connecting the cautery element to the source of the electric current.

13 Claims, 1 Drawing Sheet

RETRACTABLE ELECTRO-SUCTION DEVICE

BACKGROUND OF THE INVENTION

This invention generally relates to medical devices and, more specifically, an electrocautery device used in operative procedures.

During all laparascopic surgeries involving penetration through the abdominal wall, bleeding is usually encountered which must be stopped. For example, bleeding from the liver during gall bladder surgery has been common.

There are two devices used in most laparascopic operative procedures. The first is an electrocautery which is used to cauterize or sear tissue by burning in a surgical field. The second device is a suction tube which is used to suction blood away from the surgical field so that the bleeding can be cauterized. Both the electrocautery as well as the suction tubes are typically introduced into the abdominal cavity through trocars, well known to those skilled in the art, which are sharp-pointed surgical instruments used with a cannula to puncture a body cavity.

It is important in these procedures to clear the surgical field of as much blood as possible so as to facilitate examination by means of T.V. camera, the introduction of forceps, etc., all of which are introduced through trocars.

A prior art device is illustrated which combines a suction tube and a cautery. The problem with this device is that the cautery tip protrudes beyond the suction tube and remains in such extended position at all times while the remote free end of the device is in the abdominal cavity. This makes the instrument risky and unpopular since while the device is used for suction, the exposed cautery tip acts as a sharp instrument which can and does lacerate tissue and can have the opposite to the desired effect, namely increasing the extent of bleeding instead of decreasing bleeding.

Another known device includes a sliding mechanism which permits a surgeon to manually slide the cautery tip to an extended, active position but the cautery tip must be manually retracted. Therefore, if the surgeon forgets to retract cautery tip, this device exhibits the same disadvantages as the first mentioned fixed device.

SUMMARY OF THE INVENTION

The present invention is intended to eliminate the disadvantages inherent in prior art devices used for laparascopic surgery.

In accordance with the present invention, an electrocautery device for attachment to a suction pump and an source of electric current comprises a tubular number having two free ends. The device is connectable to the suction pump at one free end while having the other free end dimensioned and configurated to be inserted into the cavity of a human torso into proximity with bleeding vessels or tissue to suction blood in the region of the bleeding vessels or tissue, thereby improving the visibility of the bleeding vessels or tissue requiring cauterization. A cautery element is provided at the other free end which is connectable to the source of electric current for cauterizing the bleeding vessels or tissue. The cautery element is movable between a retracted position within said tubular member. In this manner, the bleeding vessels or tissue are not exposed to said cautery element. In an extended position of the cautery element, it is used for cauterization. An actuatable means is provided for selectively moving said cautery element from said retracted to said extended positions. In this manner, cauterization can be selectively performed once that cautery element is connected to the source of current upon actuation of said actuatable means to move said cautery element to said extended position.

BRIEF DESCRIPTION OF THE DRAWINGS

The manner in which the present invention is constructed and its mod of operation can best be understood from the following detailed description together with the accompanying figures in which.

DESCRIPTION OF A PREFERRED EMBODIMENT

Figure 1:
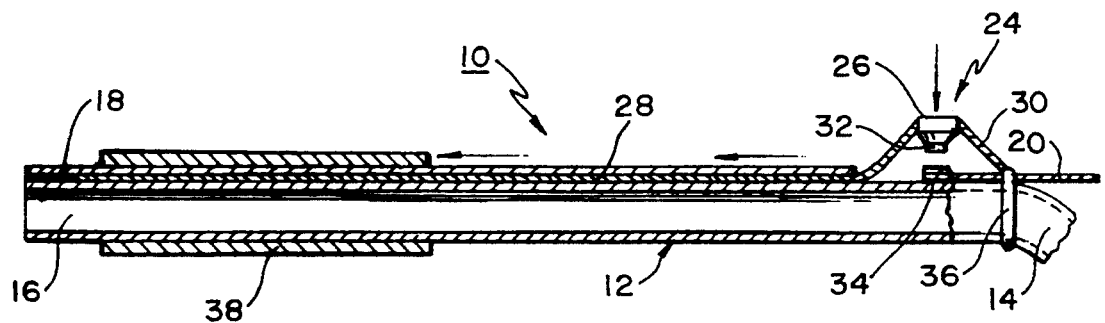
FIG. 1 is a longitudinal cross-sectional view of a retractable electro-suction device in accordance with the present invention, shown in a condition for suctioning blood but not cauterization.

Referring now to the Figures, in which the identical or similar parts are designated by the same reference numerals throughout and first referring to FIG. 1, the device in accordance to the present invention is schematically illustrated and generally designated by the reference numeral 10.

Figure 2:
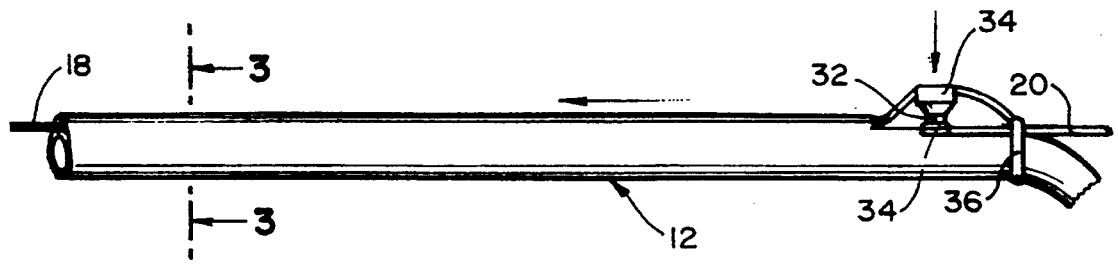
FIG. 2 is similar to FIG. 1, but showing the device manually actuated to enable the device to simultaneously cauterize and suction.
Figure 3:
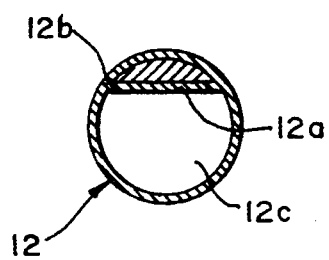
FIG. 3 is a cross-sectional view of the electro-suction device shown in FIG. 3, taken along line 4—4.

The electro-suction device 10 in accordance with the present invention includes a tubular member 12 the proximate free end 14 of which is connected to a suction pump (not shown). The remote or distal free end 16 supports a retractable cautery element or electrode 18 which can be selectively retracted or extended. In the presently preferred embodiment being described, the tubular member 12 is, referring to FIG. 3, preferably provided with a partition wall 12a which extends in the longitudinal direction at least along the distal or remote free end 16 of the tubular member 12. The partition wall 12a forms an elongate channel 12b and a suction channel 12c. The retractable cautery tip or element is slidably mounted for movements within the elongate channel 12b. An actuatable member 24 is provided which includes a manually operable button 26 which is coupled to and cooperates with an elongate link 28 which extends between the button 26 and the retractable cautery element 18. Referring to FIGS. 1 and 2, the cautery element 18 is movable between a retracted position within the elongate channel 12b and, therefore, the tubular member 12. However, the cautery element 18 can be extended by manual depression of the actuatable member 24 by manually depressing the button 26.

In the presently preferred embodiment, the actuatable member 24 also includes means for switching the electrical current and disconnecting the cautery element 16 from the source of electric current. This is achieved by placing a movable contact 32 on the lower portion of the button 26 facing the tubular member 12, and placing a fixed electrical contact 34 on the tubular member 12. The fixed electrical contact 34 is connected to the electric conductor 20 which is connected to the source of electric current 22. Referring to FIG. 2, therefore, it is noted that when the button 26 is manually depressed, the linking element or member 28 causes the cautery element 16 to advance and extend beyond the free end of the tubular member 12 while simultaneously closing the normally open switch formed by contacts 32, 34.

An important feature of the present invention is that biassing means in the form of a leaf spring 30 is utilized for maintaining the button 24 in the upper position as viewed in FIGS. 1 and 2, so that the cautery element 16 is normally and automatically retracted so that the electrical contact to the cautery element is normally open when the button 26 is released. Upon manual depression of the button 26, however, the cautery element 16 is extended and simultaneously therewith electric current is applied to the cautery element as a result of the contact between the switch contact 32, 34.

The device is intended to be used with trocars which are used in laparascopic surgery, a trocar being partially illustrated in FIG. 1 and identified by the reference numeral 38. The electro-suction device of the present invention is intended to be inserted into the abdominal cavity through or by means of a trocar.

The size of the cautery element is not critical. However, it has been found that a cautery element having a dimension in the length direction of the tubular member 12 of approximately 5–6 mm is satisfactory. Similarly, a cautery element having a dimension transverse to the length direction of the tubular element 12 of approximately 3 mm is suitable for the intended purpose. Specifically referring to FIG. 4, there is illustrated a tubular member of circular cross-section, wherein the tubular member has a diameter which is approximately 5 mm. Since trocars are typically of that diameter, the electro-suction device of the present invention needs to be dimensioned so as to be readily receivable into a trocar used in laparascopic surgery.

While the invention is described with reference to specific embodiments thereof and with respect to the incorporation therein of certain combinations of features, it is to be understood that the invention may be embodied in other forms, many of which do not incorporate all of the features present in this specific embodiment of this invention which has been described. For this reason, the invention is to be taken and limited only as defined by the claims that follow.

I claim:

1. An electrocautery device for attachment to a suction pump and to a source of electric current, comprising an elongate tubular member having first and second free ends and being connectable to the suction pump at said first free end and having said second free end dimensioned and configured to be insertable into a cavity of a human torso into proximity with bleeding vessels or tissue to suction blood in a region of the bleeding vessels or tissue thereby improving visibility of the bleeding vessels or tissue requiring cauterization; a cautery element at said second free end and connectable to the source of electric current for cauterizing the bleeding vessels or tissue, said cautery element being movable between a retracted position within said tubular member, wherein the bleeding vessels or tissue are not exposed to said cautery element, and an extended position used during cauterization; actuatable means on said elongate tubular member for selectively moving said cautery element from said retracted to said extended positions; and biassing means on said elongate tubular member and coupled to said cautery element for automatically biassing said actuatable means to normally move said cautery element to said retracted position whereby cauterization can be selectively performed when said cautery element is connected to the source of electric current upon actuation of said actuatable means to move said cautery element to said extended position while said cautery element is normally and automatically retracted when said actuatable means is released.

2. An electrocautery device as defined in claim 1, wherein an elongate channel extends along said tubular member and is dimensioned to slidably receive said cautery element.

3. An electrocautery device as defined in claim 2, wherein said tubular member has a predetermined length between said first and second free ends and said elongate channel extends substantially said entire predetermined length of said tubular member between said free ends.

4. An electrocautery device as defined in claim 2, wherein said tubular member has an interior space and said elongate channel is formed by a partition wall extending longitudinally within said tubular member to partition said interior space of said tubular member into said elongate channel and a suction channel that can be placed in fluid flow communication with the suction pump.

5. An electrocautery device as defined in claim 1, wherein said tubular member has a longitudinal axis and said cautery element has a dimension along said axis of approximately 5–6 mm.

6. An electrocautery device as defined in claim 1, wherein said actuatable means comprises an actuator at said one of said free ends, and linking means for linking said actuator with said cautery element, manual actuation of said actuator causing said cautery element to move between said retracted and extended positions.

7. An electrocautery device as defined in claim 1, wherein said biassing means comprises a leaf spring.

8. An electrocautery device as defined in claim 1, further comprising switch means for selectively connecting said cautery element to the source of current.

9. An electrocautery device as defined in claim 8, wherein said switch means is normally open.

10. An electrocautery device as defined in claim 9, wherein said switch means includes a movable contact that is mechanically coupled to said actuatable means to cause said cautery element to move to the extended position.

11. An electrocautery device as defined in claim 1, wherein said tubular member has an axis and said cautery element has a dimension transverse to said axis of approximately 3 mm.

12. An electrocautery device as defined in claim 1, wherein said tubular member is circular in cross-section.

13. An electrocautery device as defined in claim 1, wherein said tubular member has a diameter which does not exceed 5 mm.

* * * * *